United States Patent [19]
Barnette et al.

[11] Patent Number: 5,998,428
[45] Date of Patent: Dec. 7, 1999

[54] COMPOUNDS AND METHODS FOR TREATING PDE IV-RELATED DISEASES

[75] Inventors: Mary S. Barnette, West Chester; Theodore J. Torphy, Bryn Mawr; Siegfried Benjamin Christensen, IV, Philadelphia, all of Pa.

[73] Assignee: SmithKline Beecham Corporation, Philadelphia, Pa.

[21] Appl. No.: 08/944,044

[22] Filed: Sep. 3, 1997

Related U.S. Application Data

[63] Continuation of application No. 08/456,274, May 31, 1995, which is a continuation of application No. PCT/US94/06861, Jun. 17, 1994.

[51] Int. Cl.⁶ .................................................. A61K 31/44
[52] U.S. Cl. ............................................................ 514/285
[58] Field of Search ................................................ 514/285

[56] References Cited

U.S. PATENT DOCUMENTS 5,278,172  1/1994  Hennessey et al. ........................ 514/1

FOREIGN PATENT DOCUMENTS

| WO 92 00968 | 1/1992 | WIPO . |
| WO 92 19594 | 11/1992 | WIPO . |
| WO 93 19749 | 10/1993 | WIPO . |
| WO 93 19750 | 10/1993 | WIPO . |
| WO 93 19751 | 10/1993 | WIPO . |
| WO 95 24381 | 9/1995 | WIPO . |

OTHER PUBLICATIONS

J. of Pharm and Exp. Therapeutics, (1989), vol. 251, No. 1 Harris et al., Role of Low $K_m$ Cyclic AMP Phosphodiesterase Inhibition in Tracheal relaxation and bronchodiation in the Guinea pig.

Drug Development Research 21:135–142 (1990), Koe et al. Effect of Novel Catechol ether imidazolidinones on Calcium–Independent Phosphodiesterase activity, [³H]Rolipram Binding and Reserpine–induced Hypothermia in mice.

Fed. of Eur. Bio. Societies, (1992), vol. 302, No.: 2, 181–184, Souness et al., Effects of solubilization and vanadate/glutathione complex on inhibitor potencies against eosinophil cyclic AMP–specific phosphodiesterase.

P.J. Silver et al., (1990), Low $K_m$ cAMP Phosphodiesterase Isozymes and modulation of Tone in Vascular, Airway and Gastrointestinal Smooth Muscle. pp. 358–365.

Psychopharmacology (1990), 102, 17–20, Schmicchen et al., Close correlation between behavioural response and binding in vivo for inhibitors of the rolipram–sensitive phosphodiesterase.

J. Med. Chem. 1991, 34: 291–298, Saccomano et al., Calcium–Independent Phosphodiesterase Inhibitors as Putative Antidepressants: 3–(Bicycloalkyloxy)–4–methoxypheny]–2–imidazolidinones.

J. Med. Chem. 1991, 34, 86–89, Vinick et al., Nicotinamide Ethers: Novel Inhibitors of Calcium–independent Phosphodiesterase and [³H]Rolipram Binding.

Br. J. Pharmacol. (1993), 108, 562–568, Cortijo et al., Investigation into the role of phosphodiesterase IV in bronchorelaxation, including studies with human bronchus.

J. Med. Chem, 1993, 36, 1380–1386, Miyamoto et al., Bronchodilator Activity of Xanthine Derivatives Substituted with Functional Groups at the 1– or 7–Position.

J. Med. Chem. vol. 36, No. 22, Oct. 1993 pp. 3274–3277, XP002084976The Crystal structure, absolute config. And phosphodiesterase inhibitory act. Etc . . . P.W. Baures.

Trends Pharmacol. SCI, col. 12, No. 1, 1991 pp. 19–27, XP002012152, Diff. Modulation of tissue function and therapeutic potential etc.. C.D. Nicholson.

Medline. Abstract & Padiatrie Und Genzgebiete, 1991 30 (4) 327–34, Method in individualized pharm. Of diseases of the digestive and the respiratory system in children, XP002084977, M. L. Tarachowski.

*Primary Examiner*—Keith D. MacMillan
*Attorney, Agent, or Firm*—James M Kanagy; Charles M Kinzig

[57]  ABSTRACT

This invention relates to a method for selecting PDE IV inhibitors which have a salutory therapeutic index, and to compounds having these properties.

17 Claims, No Drawings

COMPOUNDS AND METHODS FOR TREATING PDE IV-RELATED DISEASES

This is a continuation of application Ser. No. 08/456,274, filed May 31, 1995, which is a continuation of PCT/US94/06861, filed Jun. 17, 1994.

SCOPE OF THE INVENTION

This invention covers compounds which preferentially inhibit, or bind, one form of a phosphodiesterase isozyme denominated IV (PDE IV hereafter) while exhibiting equal or, preferably less binding or inhibition for a second form of the enzyme. These forms, and it is believed they are different forms of non-interconvertible conformations of the same enzyme though this has not been proven, are distinguished by their binding affinity for rolipram, an architypical PDE IV inhibitor. Rolipram binds with high affinity to the catalytic site of one form but with low affinity to the catalytic site of the other. Herein one form is denominated the high affinity rolipram binding site and the other form is identified as the low affinity rolipram binding site. A method for selectively treating diseases related to inhibiting preferentially the low affinity form of the catalytic site in the PDE IV isozyme is also disclosed. A method for treating certain diseases comprising administering a compound preferentially binding to the low affinity binding site is also disclosed.

AREA OF THE INVENTION

Cyclic nucleotide phosphodiesterases (PDEs) represent a family of enzymes that hydrolyze the ubiquitous intracellular second messengers, adenosine 3',5'-monophosphate (cAMP) and guanosine 3',5'-monophosphate (cGMP) to their corresponding inactive 5'-monophosphate metabolites. At least five distinct classes of PDE isozymes are believed to exist, each possessing unique physical and kinetic characteristics and each representing a product of a different gene family. These have been distinguished using the Roman numerals I through V.

The target enzyme in this invention is the PDE IV isozyme in all its various forms and in the full domain of its distributions in all cells. It is a low $K_m$ (cAMP $K_m$=1–5 $\mu$M) cAMP-selective enzyme that has little activity against cGMP (Km>100 $\mu$M). Members of this isozyme class have the interesting characteristics of existing in two or more non-interconvertible or slowly interconvertible forms that bind rolipram and other PDE IV inhibitors with distinct rank order potencies. Thus the same gene product can exist in more than one catalytically active conformational state. Importantly, the relative proportions of the different binding forms may vary depending on the tissue cell type. For example, inflammatory cells may contain a relatively high proportion of the form that binds rolipram with a low affinity while brain and parietal cells may contain a relatively high proportion of the form that binds rolipram with a high affinity.

Of particular interest in this invention is the role this class of isozymes play in inflammation and airway smooth muscle. Studies indicate that it plays a prominent role in regulating cAMP in a wide variety of inflammatory cells (i.e., mast cells, basophils, eosinophils, neutrophils, and monocytes) and airway smooth muscle. The work of this invention is particularly applicable to inflammatory cells and airway smooth muscle; the isozyme type expressed in human monocytes is of particular interest. This is because cyclic AMP serves as a second messenger to inhibit chemotaxis and activation of inflammatory cells. In addition, cAMP mediates smooth airway muscle relaxation. This coupled with the major role of PDE IV in metabolizing cAMP has provided the underpinnings for investigating PDE IV inhibitors: by virtue of their ability to elevate cAMP content in leukocytes and airway smooth muscle, PDE IV inhibitors may posses anti-inflammatory and bronchodilator activities.

Current PDE inhibitors used in treating inflammation and as bronchodilators, drugs like theophylline and pentoxyfyllin, inhibit PDE isozymes indiscriminently in all tissues. These compounds exhibit side effects, apparently because they non-selectively inhibit all 5 PDE isozyme classes in all tissues. This is a consideration in assessing the therapeutic profile of these compounds. The targeted disease state may be effectively treated by such compounds, but unwanted secondary effects may be exhibited which, if they could be avoided or minimized, would increase the overall therapeutic effect of this approach to treating certain disease states. Taken collectively, this information suggests that the side effects associated with the use of standard non-selective PDE inhibitors might be reduced by targeting novel isozyme-selective inhibitors for the predominant PDE in the tissue or cell of interest. Although in theory isozyme-selective PDE inhibitors should represent an improvement over non-selective inhibitors, the selective inhibitors tested to date are not devoid of side effects produced as an extension of inhibiting the isozyme of interest in an inappropriate or not-targeted tissue. For example, clinical studies with the selective PDE IV inhibitor rolipram, which was being developed as an antidepressant, indicate it has psychotropic activity and produces gastrointestinal effects, e.g., pyrosis, nausea and emesis. Indications are that side effects of denbufylline, another PDE IV inhibitor targeted for the treatment of multi-infarct dementia, may include pyrosis, nausea and emesis as well. These side effects are thought to occur as a result of inhibiting PDE IV in specific areas of the CNS and gastrointestinal system.

In 1986, Schneider and colleagues described the presence and characteristics of high affinity, stereoselective [$^3$H]-rolipram binding sites in rat brain homogenates. Although it was assumed that these binding sites represented the catalytic site of the rat brain "non-calmodulin-dependent, cAMP phosphodiesterase" (i.e. PDE IV), a striking anomaly was apparent in the data. Under similar albeit not identical experimental conditions, data showed rolipram had a $K_d$=1 nM, whereas it inhibited rat brain PDE IV activity with a $K_i$=1 $\mu$M. Thus, there was a 1000-fold difference in the affinity of rolipram for the binding site versus its affect on catalytic activity. Although comprehensive structure activity relationships (SARs) for PDE inhibition and competition for [$^3$H]-rolipram binding were not established, the substantial difference in the potency of rolipram as a PDE IV inhibitor compared with its potency at the binding site seemed to question the validity of the assumption that both activities were contained within the same molecular locus.

Because of this conundrum, several studies were initiated. One sought to determine whether rolipram's high affinity binding site existed on the same protein as the cAMP catalytic site. Another study sought to determine whether or not the SAR for inhibition of PDE IV was the same as the SAR for competition with the high affinity rolipram binding site. A third study undertook to try and elucidate what biological significance, if any, there might be in these findings, particularly as it might relate to developing new drug therapies.

As data were collected from several assays, it became apparent that there are at least two binding forms on human monocyte recombinant PDE IV (hPDE IV) at which inhibitors bind. One explanation for these observations is that hPDE IV exists in two distinct forms. One binds the likes of rolipram and denbufylline with a high affinity while the other binds these compounds with a low affinity. Herein we distinguish these forms by referring to them as the high affinity rolipram binding form (HPDE IV) and the low affinity rolipram binding form (LPDE IV).

The importance of this finding lies in the discovery that compounds which potently compete for the high affinity rolipram binding form (HPDE IV) have more side effects or more intense side effects than those which more potently compete with the LPDE IV (low affinity rolipram binding form). Further data indicate that compounds can be targeted to the low affinity binding form of PDE IV and that this form is distinct from the binding form for which rolipram is a high affinity binder. Distinct SARs were found to exist for inhibitors acting at the high affinity rolipram binding form versus the low affinity rolipram binding form. In addition, these two forms appear to have different functional roles. Thus compounds that interacted with the low affinity rolipram binding form appear to have anti-inflammatory activity, whereas those that interact with the high affinity rolipram binding form produce side effects or exhibit more intensely those side effects.

There is no clear explanation for these findings. However, it is proposed the PDE IV can exist in two distinct tertiary or quaternary states. Both forms are believed to be catalytically active. Rolipram binds to one catalytic site of one form with a high affinity, defined herein as having a $K_i$ less than 10 nanomolar, and to the other form with a low affinity, defined here as having a $K_i$ of greater than 100 nanomolar.

A useful consequence of these findings is that it is now possible to identify compounds which preferentially inhibit cAMP catalytic activity where the enzyme is in the form that binds rolipram with a low affinity, thereby reducing the side effects which apparently are linked to inhibiting the form which binds rolipram with a high affinity. This provides a superior therapeutic index vis-a-vis anti-inflammatory and/or bronchodilator activities versus side effects.

SUMMARY OF THE INVENTION

In a first aspect, this invention relates to a compound which has an $IC_{50}$ ratio of about 0.1 or greater as regards the $IC_{50}$ for the PDE IV catalytic form which binds rolipram with a high affinity divided by the $IC_{50}$ for the form which binds rolipram with a low affinity.

Furthermore, this invention relates to a method for elevating cAMP in leukocytes and airway smooth muscles while minimizing gastrointestinal and psychotropic effects, which method comprises administering to a subject in need thereof an effective amount of a compound having an $IC_{50}$ ratio of about 0.1 or greater as regards the $IC_{50}$ for PDE IV catalytic form which binds rolipram with a high affinity divided by the $IC_{50}$ for the form which binds rolipram with a low affinity.

In yet another aspect, this invention relates to a method for treating inflammation or for dilating bronchi by preferentially inhibiting the PDE IV catalytic form that binds rolipram with a low affinity, which method comprises administering to a subject in need thereof a therapeutically effective amount of a compound which has an $IC_{50}$ ratio of about 0.1 or greater as regards the $IC_{50}$ for PDE IV catalytic form which binds rolipram with a high affinity divided by the $IC_{50}$ for the form which binds rolipram with a low affinity.

DETAILED DESCRIPTION OF THE INVENTION

For purposes of this invention, the cAMP catalytic site which binds rolipram with a low affinity is denominated the "low affinity" binding site (LPDE IV) and the other form of this catalytic site which binds rolipram with a high affinity is denominated the "high affinity" binding site (HPDE IV).

Initial experiments were conducted to establish and validate a [3H]-rolipram binding assay. Details of this work are given in Example 1 below.

To determine whether both the high affinity binding activity and the low affinity binding activity resided in the same gene product, yeast were transformed by known methods and the expression of recombinant PDE IV was followed over a 6 hour fermentation period. Western blot analysis using an antibody directed against PDE TV indicated that the amount of PDE IV expressed increased with time, reaching a maximum after 3 hour of growth. In addition, greater than 90% of the immunoreactive product was in the high speed (100,000×g) supernatant of yeast lysates. [$^3$H] R-(−)-Rolipram binding and PDE activity were monitored along with protein expression. PDE IV activity was co-expressed with rolipram binding activity, indicating that both functions exist on the same gene product. Similar to results with the Western plot analysis, greater than 85% of the rolipram-inhibitable PDE activity and [$^3$H]-rolipram binding activity was found to be present in the yeast supernatant fraction.

Overall, most of the recombinant PDE IV expressed in this system exists as LPDE IV and only a small fraction as HPDE IV. Consequently, inhibition of recombinant PDE IV catalytic activity primarily reflects the actions of compounds at LPDE IV. Inhibition of PDE IV catalytic activity can thus be used as an index of the potency of compounds at LPDE IV. The potency of compounds at HPDE IV can be assessed by examining their ability to compete for [$^3$H]R-rolipram. To develop SARs for both the low affinity and high affinity rolipram binding sites, the potencies of selected compounds were determined in two assay systems. Results from experiments using standard compounds were tabulated. As expected, certain compounds were clearly more potent in competing with [$^3$H]-rolipram at the site for which rolipram demonstrated high affinity binding as compared with the other site, the one at which rolipram is a low affinity binder. SAR correlation between high affinity binding and low affinity binding was poor and it was concluded that the SAR for inhibition of high affinity [$^3$H]-rolipram binding was distinct from the SAR for binding to the low affinity rolipram binding site. Table I provides results from this SAR work.

TABLE I

| Compound | Low Affinity $IC_{50}$ | High Affinity $IC_{50}$ | High/Low Ratio |
| --- | --- | --- | --- |
| 1-(5-tetrazole)-3-(3-cyclopentyloxy-4-methoxyphenyl)cyclopentane | 1.1 | 0.002 | 0.0018 |
| cis-[3-(3-cyclopentyloxy-4-methoxyphenyl)cyclopentane-1-carboxylate] | 2.7 | 0.021 | 0.0078 |
| N-[2-(3-cyclopentyloxy-4-methoxyphenyl)ethyl]oxamide | 0.89 | 0.012 | 0.013 |
| R-rolipram | 0.31 | 0.004 | 0.013 |
| N-[2-(3,4-bisdifluoromethoxyphenyl)ethyl]oxamide | 1.6 | 0.04 | 0.25 |
| Ro 20-1724 | 2.6 | 0.095 | 0.07 |

TABLE I-continued

| Compound | Low Affinity IC$_{50}$ | High Affinity IC$_{50}$ | High/Low Ratio |
|---|---|---|---|
| S-rolipram | 1.1 | 0.95 | 0.07 |
| (R)-(+)-1-(4-bromobenzyl)-4-[(3-cyclopentyloxy)-4-methoxyphenyl]-2-pyrrolidone | 4.0 | 0.45 | 0.11 |
| 1-(4-aminobenzyl)-4-(3-cyclopentyloxy-4-methoxyphenyl)-2-imidazolidinone | 1.4 | 0.01 | 0.07 |
| denbufylline | 0.29 | 0.05 | 0.17 |
| 3-(cyclopentyloxy-4-methoxyphenyl)-1-(4-N'-[N2-cyano-S-methyl-isothioureido]benzyl)-2-pyrrolidone | 0.1 | 0.03 | 0.30 |
| (R)-(+)-1-(4-bromobenzyl)-4-[(3-cyclopentyloxy)-4-methoxyphenyl]-2-pyrrolidone | 0.06 | 0.02 | 0.33 |
| IBMX | 29.1 | 20.3 | 0.698 |
| (S)-(-)-ethyl [4-(3-cyclopentyloxy-4-methoxyphenyl)pyrrolidine-2-ylidene]acetate | 0.46 | 0.45 | .98 |
| Papaverine | 10 | 10 | 1.0 |
| cis-[4-cyano-4-(3-cyclopentyloxy-4-methoxyphenyl)cyclohexan-1-carboxylate] | 0.095 | 0.110 | 1.1 |
| cis-[4-cyano-4-(3-cyclopropylmethoxy-4-difluoromethoxyphenyl)cyclohexan-1-ol] | 0.021 | 0.04 | 2.0 |
| (R)-(+)-ethyl[4-(3-cyclopentyloxy-4-methoxyphenyl)pyrrolidine-2-ylidene]acetate | 0.14 | 0.3 | 2.143 |
| 2-carbomethoxy-4-cyano-4-(3-cyclopropylmethoxy-4-difluoromethoxyphenyl)cyclohexan-1-one | 0.140 | 0.5 | 3.571 |
| trequinsin | 1.6 | 5.0 | 3.125 |
| dipyridamole | 5.2 | 32.5 | 6.25 |

Denbufylline is 7-acetonyl,1,3-dibutylxanthine made by SmithKline Beecham. Papaverine is 1-[(3,4-dimethoxyphenyl)methyl]-6,7-dimethoxyisoquinoline. Trequinsin is 2,3,6,7-tetrahydro-2-(mesitylimino)-9,10-dimethoxy-3-methyl-4H-primido[6,1-α]isoquinoline-4-one. Dipyrimadole is the generic name for 2,2',2''2'''-[(4,8-dipiperidinopyrimido[5,4-d]pyrimidine-2-6-diyl)dinitrilo]tetraethanol.

These results illustrate that some compounds can selectively inhibit the so called low affinity form as compared with the high affinity form, and vice versa. The significance of this finding is that it is feasible to minimize side effects by designing or choosing compounds which selectively (preferentially) inhibit one site thereby affecting the desired response to the exclusion of another, unwanted, response, or at least to minimize the non-targeted response to a degree where it is not interfering with the intended therapy to an unacceptable degree.

Notwithstanding this work, we have not defined the basis for the disparate SARs for high affinity rolipram binding and low affinity rolipram binding in the PDE IV isozyme,. However it has been discovered that if a compound exhibits an IC$_{50}$ ratio of about 0.1 or greater, calculated as the ratio of the IC$_{50}$ for high affinity rolipram binding form divided by the IC$_{50}$ for the form which binds rolipram with a low affinity, it will have an acceptable therapeutic index. That is, one can now successfully treat a variety of immune and inflammatory diseases while not affecting other physiological phenomena at all or to an unacceptable degree. Herein the most preferred embodiment is inhibiting the low affinity rolipram binding site as a means for treating inflammatory and allergic diseases.

Compounds

This invention covers those compounds which have an IC$_{50}$ ratio (high/low binding) of about 0.1 or greater. This includes any and all compounds which are PDE IV inhibitors as per the test set our herein, and which demonstrate in these, or similar assays, a ratio within the defined range; of particular interest are those compounds which are not in the public domain and/or not tested as or known to be PDE IV inhibitors prior to the filing date of this application.

Examples of compounds which meet the IC$_{50}$ ratio standard are given in Table 1 above as well as pending U.S. patent applications U.S. Ser. No. 862,083 filed Oct. 30, 1992; U.S. Ser. No. 862,111 filed Oct. 30, 1992; U.S. Ser. No. 862,030 filed Oct. 30, 1992; and U.S. Ser. No. 862,114 filed Oct. 30, 1992. Each of these applications is incorporated herein by reference in full as if set out in this document.

Preferred compounds of this invention are those which have an IC$_{50}$ ratio of greater than 0.5, and particularly those compounds having a ratio of greater than 1.0. Preferred compounds are trequinsin, dipyridamole, and papaverine. Compounds such as cis-[cyano-4-(3-cyclopentyloxy-4-methoxyphenyl)cyclohexan-1-carboxylate], 2-carbomethoxy-4-cyano-4-(3-cyclopropylmethoxy-4-difluoromethoxyphenyl)cyclohexan-1-one, and cis-[4-cyano-4-(3-cyclopropylmethoxy-4-difluoromethoxyphenyl)cyclohexan-1-ol] are examples of structures which bind preferentially to the low affinity binding site and which have an IC$_{50}$ ratio of 0.1 or greater.

The following examples are provided to illustrate how to make and use the invention.

They are not in any way intended to limit the scope of the invention in any manner or to any degree. Please refer to the claims for what is reserved to the inventors hereunder.

EXAMPLES

Eight different assays spread among five species were used to develop data supporting the selection of an IC$_{50}$ ratio of about 0.1 or greater. The assays were: stimulation of acid production from rabbit isolated parietal gland; inhibition of FMLP-induced degranulation (release of myleoperoxidase) in human neutrophils; inhibition of FMLP-included O$_2^-$ formation in guinea pig eosinophils; inhibition of LPS-induced TNF$_\alpha$ production in human monocytes; production of emesis in dogs; inhibition of antigen-induced bronchoconstriction in guinea pigs; reversal of reserpine-induced hypothermia in mice; and inhibition of LPS-induced TNF$_\alpha$ production from adoptively-transferred human monocytes in mice. These assays and data are presented below.

Statistical Analysis

To examine the hypothesis that inhibition of the low affinity site PDE IV is associated with the anti-inflammatory actions of this class of compounds, whereas inhibition of the high affinity site is associated with the production of certain side effects, we determined the ability of various PDE IV inhibitors to block inflammatory cell function both in vitro and in vivo and the ability of these compounds to produce side effects in in vitro and in vivo models. To compare the ability of PDE IV inhibitors to elicit a given therapeutic effect or side effect with their ability to inhibit the low affinity binding site versus their ability to inhibit the high affinity site of PDE IV, we compared the potency of these compounds in the in vitro or in vivo assays with their potency against the isolated enzyme catalytic activity or the high affinity site by a linear correlation of ($r^2$) or a rank order correlation (Spearman's Rho). The linear correlation asks whether the potency of a compound at inhibiting either the low affinity site or the high affinity site can be used to predict the ability to elicit a given anti-inflammatory or side effect.

The rank order correlation tests whether the rank order potency in producing a given anti-inflammatory or side effect is similar to the rank order potency in inhibiting the low affinity or the high affinity site. Both $r^2$ and Spearman's Rho were calculated using the STAT View II computer program for the Macintosh.

PDE IV versus Rolipram High Affinity Binding

Example 1

Phosphodiesterase and Rolipram Binding Assays

Isolated human monocyte PDE IV and HPDE IV was determined to exist primarily in the low affinity form. Hence, the activity of test compounds against the low affinity form of PDE IV can be assessed using standard assays for PDE IV catalytic activity employing 1 $\mu$M [$^3$H]cAMP as a substrate (Torphy et al., 1992).

Rat brain high speed supernatants were used as a source of protein and both enantionmers of [$^3$H]-rolipram were prepared to a specific activity of 25.6 Ci/mmol. Standard assay conditions were modified from the published procedure to be identical to the PDE assay conditions, except for the last of the cAMP: 50 mM Tris HCl (pH 7.5), 5 mM $MgCl_2$, 50 $\mu$M 5'-AMP and 1 nM of [$^3$H]-rolipram (Torphy et al., 1992). The assay was run for 1 hour at 30° C. The reaction was terminated and bound ligand was separated from free ligand using a Brandel cell harvester. Competition for the high affinity binding site was assessed under conditions that were identical to those used for measuring low affinity PDE activity, expect that [$^3$H]-cAMP was not present.

Example 2

Aminopyrine Accumulation

Certain methylxanthines and other non-selective PDE inhibitors increase acid secretion in a variety of species. Certain selective PDE IV inhibitors, e.g., rolipram and Ro 20-1724, enhance acid secretion in rats, particularly when given in combination with an activator of adenylate cyclase such as histamine. This increase in acid secretion is accompanied by an elevation of histamine-induced cAMP accumulation. This reported information was rested to determine if the phenomena existed. The ability of compounds to induce acid secretion was correlated with their ability against the low affinity site or the high affinity site. The assay used in this work was the accumulation of a weak base, radiolabeled aminopyrine which has been reported to serve as a biochemical marker for increased acid secretion. The assay follows:

Gastric Gland Preparation

Rabbits of either sex were euthanized by cervical dislocation and the stomach removed. The mucosa was dissected from the corpus; the cranial and antral portions of the stomach were discarded. Gastric glands were isolated by a modification of the methods described by Berglindh and Obrink (1976) and Sack and Spenney (1982). The mucosa was then minced and digested with collagenase to isolate the gastric glands. The digested glands were filtered, washed, and resuspended 1:15 (vol:vol) in incubation medium of the following composition: NaCl, 132.4 mM; KCl, 5.4 mM; $Na_2HPO_4$, 5.0 mM; $NaH_2PO_4$, 1.0 mM; $MgSO_4$, 1.2 mM; $CaCl_2$, 1.0 mM; $NaHCO_3$, 12.0 mM; rabbit serum albumin, 2 mg/ml; dextrose, 2 mg/ml; at a pH 7.4.

Aminopyrine Accumulation

To determine acid secretion, the gastric glands in combination with [$^{14}$C]-aminopyrine, various concentrations of selective PDE IV inhibitors, and a threshold concentration of histamine (0.3–1.0 $\mu$M) were incubated at 37° C. on a horizontal shaker (110 cycles/min) for 20 minutes according to the procedures of Sack and Spinney (1982). Samples were then centrifuged and radioactivity in aliquots of the supernatant fraction and pellet were determined. Aminopyrine ratios were calculated as described by Sack and Spenney (1982). The data were expressed as a percent of a response produced by a maximal concentration of histamine (100 $\mu$M). $EC_{50}$ values were determined by linear interpolation using the maximum response obtained for each compound.

Example 3

Evaluation of the Emetic Potential of Selective PDE Inhibitors in Dogs

Mongrel dogs (n=5, for each study) of either sex were obtained from the animal colony. After an overnight fast, the dogs were fed ½ can of dog food (Big Bet) at least 30 minutes prior to study. A cannula was placed in the cephalic vein of either foreleg to administer drugs. The cannula was flushed with 1 ml of isotonic saline (0.9%) prior to administration of the experimental compound. Compounds were dissolved in either a mixture of polyethylene glycol and saline or 100% polyethylene glycol and given at a volume of 1.0–2.0 ml/10 kg. To insure that the entire dose entered the circulation, the cannula was flushed with additional 0.5–1.0 ml of saline. The animal was returned to a cage for a 1 hour observation period. Each dog was observed for signs of retching or vomiting and the time after administration of compound for the occurrence of this behavior was noted. At the end of the observation period, the animal was returned to its home cage. Each study day was separated by 7 days. Each compound was administered in ascending doses to each dog on successive study days until an emetic effect was observed. At this time, the individual dog was dropped from the study and higher doses were evaluated in only those dogs that had not yet responded.

The data were expressed as the cumulative percent of dogs responding at each dose as described in the literature for quantal dose response curves. An $ED_{50}$ value was calculated using probit analysis.

Example 4

Guinea Pig Eosinophil Assay

Eosinophil Isolation and Purification

Male (Hartley, Hazelton Labs) guinea pigs were injected with 1 ml of horse serum weekly for 4–6 weeks prior to use. Animals were anesthetized with a mixture of ketamine/xylazine (88 mg; 12 mg/ml; 0.4 ml/kg at least 24 hrs after an injection of horse serum. After the induction of anesthesia the peritoneal cavity was lavaged with 50 ml of warm sterile saline (0.9%). The lavage fluid was collected using a 14 G catheter into 50 ml plastic conical centrifuge tubes. The guinea pigs were allowed to recover from the anesthesia and could be used again after a two-week rest period.

Cells were isolated from the lavage fluid by centrifugation (400×g, 10 min) and were resuspended in 35 ml of phosphate buffered saline (PBS) and underlayed with 10 ml of isotonic Percoll (1.075 g/ml). This suspension was centrifuged for 30 min at 300×g. The pellet containing mainly eosinophils and erythrocytes was washed in PBS and the erythrocytes lysed. These cells were resuspended in RPMI 1640 medium with 20% FBS and incubated overnight at 37° C. in a humidified 5% $CO_2$ incubator. The next day cells were washed and resuspended in PBS for determination of cell viability (trypan blue exclusion) and purity.

Superoxide Anion Production ($O_2^-$)

Purified eosinophils (viability>95% and purity>90%) were resuspended in PBS with 20 mM HEPES Buffer (pH 7.4) and 0.1% gelatin at a concentration 1–2×10$^6$ cell/ml.

Eosinophils ($1\times10^5$) were added to a 96 well plate and were incubated for approximately 1 hr at 37° C. PDE IV inhibitors were added for 10 min prior to the start of the reaction. The reaction was initiated by the addition of cytochrome C (160 $\mu$M) and formylMet-Leu-Phe (fMLP) (30 nM) in the absence or presence of 60 units of superoxide dismutase (SOD). Cytochrome C reduction was monitored on a Dynatech MR 7000 plate reader at 550 nm with a 630 nm reference at various time periods. The rate of $O_2^-$ production was determined by linear regression analysis using the net absorbance of wells in the absence or presence of SOD at several time points. Results were expressed as a percent of the control production of $O_2^-$ corrected for basal release. Sine the maximal inhibition observed was 60%, log $IC_{30}$ were calculated using linear interpolation of the concentration and bracketing 30%.

Example 5
Bronchoconstriction in Guinea Pigs

Male Hartley guinea pigs (200–250 g/4 weeks, Hazelton Research, Denver, Pa.) were sensitized by I.M. injections of 0.35 ml of a 5% (w/v) ovalbumin/saline solution into each thigh (0.7 ml total) on Days 1 and 4. Guinea pigs were available for use after day 25.

Experimental Procedure

Male Hartley guinea pigs (600–800 g Hazelton), actively sensitized to ovalbumin, were anesthetized with sodium pentobarbital (40 mg/kg I.P.) approximately 10–15 minutes prior to surgery. The jugular vein, carotid artery, and trachea were cannulated (Deseret Intracath® Vialon® polymer resin radiopaque catheters (Deseret Medical, Inc., Sandy, Utah), 22 GA and 19 GA, and PE tubing 260, respectively) for drug administration, blood pressure monitoring and ventilation. Bilateral vagotomy was performed to minimize cholinergic interference. Animals were paralyzed (pancuronium bromide, 0.1 mg/kg i.v.) and ventilated (45 breaths/min) via a Harvard Rodent Respirator (model 683, Harvard Apparatus, South Natick, Mass.). Airway pressure changes were measured via a side-arm of the tracheal cannula with a Elcomatic transducer (Buxco Electronics, Sharon, Conn.). The ventilatory stroke volume was set to produce a side arm pressure of 8 cm of $H_2O$ (ca 5 cc room air). Blood pressure was measured with a Statham P23XL Physical Pressure Transducer (Viggo-Spectramed, Oxnard, Calif.). Pressures were recorded on a Grass Model 7D Polygraph (Grass Instrument Co., Quincy, Mass.). The animals were kept warm on a heating table throughout the experiment to maintain body temperature.

Test compounds or vehicle were administered via the i.v. route 10 minutes prior to antigen challenge. At the 0 time point, 0.1 mg/kg ovalbumin is administered via the i.v. route. At the peak of the antigen response, an additional dose of antigen, 0.2 mg/kg ovalbumin, i.v. was administered After the peak antigen response to the cumulative 0.3 mg/kg ovalbumin was reached, a saturated KCl solution, 1 cc/kg, i.v., was administered which produced maximal bronchoconstriction.

Example 6
Inhibition of LPS-Induced $TNF_\alpha$ in Human Monocytes
In Vitro Studies To determine whether $TNF_\alpha$ inhibition is related to inhibition of LPDE IV or HPDE IV, a series of PDE IV inhibitors having a range of potencies for the LPDE IV and HPDE IV were screened for their ability to inhibit $TNF_\alpha$ production in human monocytes stimulated with lipopolysaccharides (LPS) in vitro. The use of primary human cells for this screen was deemed to be extremely important given that different species appear to differ dramatically in the relative contribution of LPDE IV and HPDE IV to cAMP hydrolysis in inflammatory cells.

Methods $TNF_\alpha$ inhibition was assessed in human peripheral blood monocytes which were purified (Collata) from freshly obtained buffy coats or plasma-phoresis residues of blood from normal human donors. Monocytes were plated at density of $1\times10^6$ cells/ml medium/well in 24-well multi-dishes. The cells were allowed to adhere for 1 hr, after which time the supernatant was aspirated and 1 ml of fresh medium (RPMI-1640 containing 1% fetal calf serum and penicillin/streptomycin at 10 U/ml) was added. The cells were incubated for 45 min in the presence or absence of test compounds at concentrations ranging from 1 nM to 1 mM prior to the addition of LPS (E. coli. 055:B5, Sigma Chemicals) to yield a final concentration of 100 ng/ml. Test compounds were solubilized and diluted in a 50:50 concentration of dimethylsulfoxide/ethanol, such that the final solvent concentration in monocyte culture medium was 0.5% dimethylsulfoxide and 0.5% ethanol. Culture supernants were removed from the monocytes after 14–16 hr incubation at 37° C./5%$CO_2$, and centrifuged at 100×G to remove cell debris. Cytokine assays were performed either immediately or culture supernatants were stored at −70° C. until assayed Levels of $TNF_\alpha$ were measured using a ELISA (Winston) employing a murine monoclonal anti-human $TNF_\alpha$ antibody (see below) as the capture antibody and a polyclonal rabbit antihuman $TNF_\alpha$ as the second antibody. For detection, a peroxidase-conjugated goat anti-rabbit (Boehringer Mannheim, Cat. #605222) was added followed by a substrate for peroxidase (1 mg/ml orthophenylenediamine with 0.1% urea peroxide). $TNF_\alpha$ levels in samples were calculated from a standard curve generated with recombinant human $TNF_\alpha$ produced in E. coli. Monoclonal antibodies to human $TNF_\alpha$ were prepared from spleens of BALB/c mice immunized with recombinant human $TNF_\alpha$ by a modification of the method of Kohler and Millstein (Nature, vo. 256, p495–497, 1975). Polyclonal rabbit anti-human $TNF_\alpha$ antibodies were prepared by repeated immunization of New Zealand white rabbits with recombinant human $TNF_\alpha$ emulsified in complete Freund's adjuvant.

In Vivo Suppression of Human $TNF_\alpha$ Production in an Adoptive Peritonitis Model Methods One half unit of heparinized venous whole blood was drawn from healthy employees who were not taking any kind of medication. Polymorphonuclear luekocytes were separated by layering the blood on Histopaque-1077 with centrifugation at 800×g for 30 min at 25° C. The lymphocyte/monocyte portion was harvested and washed twice with DPBS (Dulbecco's phosphate buffered saline) without $Ca^{2+}$ and $Mg^{2+}$ at 1000 rpm for 10 min at 25° C. The pellet was resuspended in 5 ml of DPBS without $Ca^{2+}$ and $Mg^{2+}$, layered on 5 ml Percoll solution prepared in RPMI 1640 medium which was devoid of serum at 25° C., and centrifuged at 550×g for 30 min at 25° C. The buoyant layer of monocytes was removed and washed twice with DPBS without $Ca^{2+}$ and $Mg^{2+}$ at 1000 rpm for 10 min at 25° C. The final washed monocyte isolate was suspended at $6-10\times10^6$ cells/ml in DPBS without $Ca^{2+}$ and $Mg^{2+}$ at 25° C. Monocytes were also isolated by the same procedure from Source Leukocytes packs. The monocyte preparations ranged from 65 to 90% monocytes and the viability of the cells was >97% (trypan blue exclusion).

BALB/c male (Charles River Laboratories, Wilmington, Mass.) in groups of 4 or 5, were maintained in a barriersustained facility. Mice weighting 18–25 g and of the same age were injected with 0.5 ml of 6–10×10$^6$ monocytes/ml into the peritoneum using light pressure on a syringe with a 23 ga needle so that the monocytes were exposed to minimal shearing forces and stress. Within 2 min of receiving monocytes, the mice were treated with vehicle or compound by oral dosing for 15 min. The animals were then injected intraperitoneally (i.p.) with 0.2 ml of 125 mg/ml of endotoxin (*E. coli.*, type W, Difco) dissolved in DPBS without Ca$^{2+}$ and Mg$^{2+}$. Two hr later, the animals were euthanized by carbon dioxide asphyxiation and 1.5 ml of DPBS without Ca$^{2+}$ and Mg$^{2+}$ (4° C.) was injected i.p. The peritoneum was gently massaged and the wash was removed and placed in polyproylene tubes in an ice bath. The samples were clarified by centrifugation (12,500×g for 5 min at 4° C.). The supernatants were decanted into new tubes (may be stored at –20° C.) and assayed for human and mouse TNF$_\alpha$ by ELISAs. ED$_{50}$ values were calculated by standard procedures.

Example 7
Human Neutrophils Methods
Isolation and Purification

Neutrophils (PMNs) were isolated from heparinized blood by gradient centrifugation using Ficoll (Histopaque 1077) followed by dextran sedimentation to remove the erythrocytes. Any remaining erythrocytes were lysed with water for 30 sec and isotonicity restored using 10×DB-PBS (w/o Ca$^{2+}$ or Mg$^{2+}$). PMNs were isolated by centrifugation and were washed one additional time with 1×DB-PBS prior to determining cell number and viability (trypan blue dye exclusion). Cell number was adjusted to 0.75–1.5×10$^6$ cells/ml depending on the individual donor.
Degranulation (Release of Myleoperoxidase)

An aliquot (0.1 ml) of the above cell suspension was incubated in Earles Balanced Salt Solution containing 20 mM HEPES buffer (pH=7.4) and 0.1% gelatin in the presence of 5 μg/ml of cytochalasin B for 5 min at 37° C. in a shaking water bath. Cells were pretreated for additional 5 min with various concentrations of selective PDE IV inhibitors and PGE$_2$ (3–10 nM) prior to addition of fMLP (30 nM). fMLP was added and the incubation continued for an additional 30 min. The reaction was terminated by placement of the samples on ice followed by centrifugation. The supernatant fraction was removed and stored frozen (–30° C.) until assay for myeloperoxidase activity.
Determination of Myeloperoxidase Activity Myeloperoxidase activity was determined using o-dianisidine as substrate and horseradish peroxidase as a standard. An aliquot (50 μl) of supernatant was incubated with 100 μl of substrate (o-dianisidine, 0.53 mM; H$_2$O$_2$, 0.147 mM; final concentration) in 50 mM Na Phosphate buffer (pH 6.0). The reaction was terminated by the addition of 50 μL of 4 M H$_2$SO$_4$. Product formation was determined by measuring absorbance at 410 nm and activity determined by comparison to the standard curve using horseradish peroxidase. Data were expressed as percent of control (amount of myeloperoxidase released in the presence of PGE$_2$ alone). Since the maximal inhibition observed for the majority of compounds was 30%, log (IC$_{15}$) values were calculated using linear interpolation of the concentrations bracketing 15%.

Example 8
Reversal of Reserpine-Induced Hypothermia in Mice

Male CF-1 or BALB/c mice were individually isolated in wire cages. The rectal temperature of each mouse was recorded prior to pretreatment with reserpine (10 mg/kg, i.p.). Four hours after reserpine the rectal temperatures were recorded and individual animals were given various doses (orally) of either test compounds, vehicle, or rolipram (10 mg/kg). Rectal temperatures were then recorded every 30 min for 2 hr. The data were expressed as the change in temperature from that observed at four hrs post reserpine (temperatures dropped approximately 10–15° C. below basal levels). Dose-response curves were constructed using temperature changes recorded at 90 or 120 min after treatment. ED$_{50}$ values were determined by probit analysis or linear regression of the means of 6–9 animals. To compare the ability of compounds to reverse reserpine-induced hypothermia with their ability to inhibit low affinity binding or high affinity binding, the ED$_{50}$ and IC$_{50}$ values were expressed as –log (value).

Example 9
Relationship Between Biological Function and Inhibition of PDE IV

To determine if certain biological effects of PDE IV inhibition were associated with inhibition of either the LPDE IV or HPDE IV a comparison between the ability of compounds to produce an effect and the ability of compounds to inhibit LPDE IV or HPDE IV was determined using a linear and rank order correlation. These correlations can be influenced by several factors: 1) the stability of compounds; 2) ability of compounds to enter cells; 3) in in vivo studies, the bioavailability of compounds; 4) the correlation values, especially the linear correlation are sensitive to the difference in potencies, the greater the range of potency values the easier it is to measure a significant linear correlation. These caveats were taken into consideration when analyzing and summarizing the correlation between inhibition of LPDE IV or HPDE IV and the biological function in the various assay systems.

Using isolated inflammatory cells, suppression of monocyte TNF$_\alpha$ production and inhibition of superoxide production in guinea pig eosinophils was better correlated with inhibition of LPDE IV and not HPDE IV. Furthermore, prevention of antigen-induced bronchoconstriction in vivo was better correlated with inhibition of LPDE TV than HPDE IV. In this in vivo model, PDE IV inhibitors appear to act by preventing mast cell degranulation (Underwood et al., in press). However, inhibition of inflammatory cell function was not always associated with inhibition of LPDE IV because it was found that inhibition of neutrophil degranulation was better correlated with inhibition of HPDE IV than LPDE IV. Thus it appears that some but not all suppression of inflammatory cell activity was associated with inhibition of LPDE IV. In contrast, enhancement of acid secretion, production of emesis and reversal of resperpine-induced hypothermia (a measure of the psychtropic potential of PDE IV inhibitors) were better correlated with inhibition of HPDE IV and not LPDE IV. Thus most of the potential side effects of this class of compounds were associated with inhibition of HPDE IV.

Thus these findings suggest that compounds which preferentially inhibit LPDE IV will produce beneficial anti-inflammatory effects with reduced potential to elicit unwanted side effects. Thus selecting compounds with an IC$_{50}$ ratio of about 0.1 or greater as regards the IC$_{50}$ for PDE IV catalytic form which binds rolipram with a high affinity divided by the IC$_{50}$ for PDE IV catalytic form which binds rolipram with a low affinity (HPDE IV/LPDE IV) should result in an increase in their therapeutic index, i.e., the salutory effect is maximized and the deleterious effect is minimized.

To determine if this selection guide would indeed identify compounds with an improved therapeutic index, three models comparing a therapeutic effect with a side effect were evaluated These included an in vitro comparison between the ability of compounds to suppress TNFα production from isolated human monocytes with their ability to stimulate acid secretion in isolated rabbit parietal glands and two in vivo comparisons examining the ability of compounds to prevent antigen-induced bronchoconstriction in guinea pigs and the ability to elicit emesis in dogs and the ability of compounds to suppress TNFα production in an adoptive transfer model in mice and their ability to reverse reserpine-induced hypothermia in mice.

PDE IV inhibitors with a selectivity ratio (HPDE IV/LPDE IV) of equal to or greater than 0.1 showed a marked improvement in their therapeutic index. For example, cis-[4-cyano-4-(3-cyclopentyloxy-4-methoxyphenyl)cyclohexan-1-carboxylate], 2-carbomethoxy-4-cyano-4-(3-cyclopropylmethoxy-4-difluoromethoxyphenyl)cyclohexan-1-one, and cis-[4-cyano-4-(3-cyclopropylmethoxy-4-difluoromethoxyphenyl) cyclohexan-1-ol] all with selecitivy ratio of $\geq 0.1$ demonstrate a 100×fold improvement in their therapeutic index in comparison with the archetypal PDE IV inhibitor, R-rolipram. Thus, this demonstrates that using the selection guide of HPDE IV $IC_{50}$/LPDE IV $IC_{50} \geq /0.1$ identifies compounds with an increased therapeutic index in vitro comparison.

We claim:

1. A method for identifying a PDE IV inhibitor useful for treating inflammation while minimizing gastrointestinal and psychotropic effects, which method comprises determining for said inhibitor the $IC_{50}$ for its binding with the PDE IV form which binds rolipram with a high affinity and its $IC_{50}$ for its binding with the PDE IV form which binds rolipram with a low affinity, and determining whether the ratio of high affinity to low affinity $IC_{50}$s is about 0.1 or greater.

2. The method of claim 1 wherein the method identifies an inhibitor which has an $IC_{50}$ ratio of about 0.1 or greater as determined by using rat brain PDE IV as the form which binds rolipram with a high affinity and human PDE IV as the form which binds rolipram with a low affinity.

3. The method of claim 1 wherein the low affinity binding form of PDE IV is derived from human monocytes.

4. The method of claim 1 wherein the low affinity binding form of PDE IV is a recombinant human PDE IV.

5. The method of claim 1 wherein the PDE IV is from a tissue cellular or recombinant source.

6. The method of claim 1 wherein the PDE IV used as the high affinity binding form of PDE IV is the high-speed supernatant of a rat brain cell homogenate.

7. The method of claim 1 wherein the PDE IV is a recombinant protein.

8. The method of claim 1, 2, 3, 4, 5, 6 or 7 wherein the $IC_{50}$ ratio is about 0.5 or greater.

9. The method of claim 1, 2, 3, 4, 5, 6 or 7 wherein the $IC_{50}$ ratio is about 1.0 or greater.

10. A method for identifying a PDE IV inhibitor useful as a bronchodilator while minimizing gastrointestinal and psychotropic effects, which method comprises determining for said inhibitor the $IC_{50}$ for its binding with the PDE IV form which binds rolipram with a high affinity and its $IC_{50}$ for its binding with the PDE IV form which binds rolipram with a low affinity, and determining whether the ratio of high affinity to low affinity $IC_{50}$s is about 0.1 or greater.

11. The method of claim 10 wherein the PDE IV is from a tissue cellular or recombinant source.

12. The method of claim 10 wherein the method identifies an inhibitor which has an $IC_{50}$ ratio of about 0.1 or greater as determined by using rat brain homogenate as the source of PDE IV for the form which binds rolipram with a high affinity and a human monocytes homogenate as the source of PDE IV for the form which binds rolipram with a low affinity.

13. The method of claim 10 wherein the PDE IV is a recombinant human PDE IV.

14. The method of claim 10 wherein the PDE IV used as the high affinity binding form of PDE IV is derived from the high-speed supernatant of a rat brain cell homogenate.

15. The method of claim 10 wherein the PDE IV is a recombinant protein.

16. The method of claim 10, 11, 12, 13, 14, or 15 wherein the $IC_{50}$ ratio is about 0.5 or greater.

17. The method of claim 10, 11, 12, 13, 14, or 15 wherein the $IC_{50}$ ratio is about 1.0 or greater.

* * * * *